United States Patent [19]
Smedley et al.

[11] Patent Number: 5,380,296
[45] Date of Patent: Jan. 10, 1995

[54] MULTI-CELLED SAFETY PACKAGE, NEEDLE GUARD AND SAFE DISPOSAL MODULE FOR PRE-FILLED MEDICATION CARTRIDGES

[75] Inventors: William H. Smedley, Lake Elsinore; Terry M. Haber, Lake Forest; Clark B. Foster, Laguna Niguel, all of Calif.

[73] Assignee: Sterling Winthrop Inc., Malvern, Pa.

[21] Appl. No.: 259,289

[22] Filed: Jun. 13, 1994

Related U.S. Application Data

[60] Division of Ser. No. 153,945, Nov. 16, 1993, Pat. No. 5,324,272, which is a continuation of Ser. No. 973,582, Nov. 6, 1992, abandoned, which is a continuation of Ser. No. 558,878, Jul. 27, 1990, abandoned.

[51] Int. Cl.6 ............................................. A61M 5/32
[52] U.S. Cl. .................................... 604/193; 604/232
[58] Field of Search ............................ 604/192–199, 604/232, 234, 263, 110

[56] References Cited

U.S. PATENT DOCUMENTS

| | | |
|---|---|---|
| 2,888,923 | 6/1959 | Da Cunha Reis . |
| 2,925,083 | 2/1960 | Craig . |
| 3,356,089 | 12/1967 | Francis . |
| 3,820,652 | 6/1974 | Thackston . |
| 3,916,893 | 11/1975 | De Felice . |
| 4,507,117 | 3/1985 | Vining et al. . |
| 4,592,744 | 6/1986 | Jagger et al. . |
| 4,790,822 | 12/1988 | Haining . |
| 4,808,169 | 2/1989 | Haber et al. . |
| 4,826,489 | 5/1989 | Haber et al. . |
| 4,834,717 | 5/1989 | Haber et al. . |
| 4,846,796 | 7/1989 | Carrell et al. . |
| 4,865,592 | 9/1989 | Rycroft . |
| 4,888,002 | 12/1989 | Braginetz et al. . |
| 4,909,794 | 3/1990 | Haber et al. . |
| 4,919,652 | 4/1990 | Alter et al. . |
| 4,932,945 | 6/1990 | Braginetz et al. . |
| 4,950,251 | 8/1990 | Haining . |
| 5,324,272 | 6/1994 | Smedley et al. ............... 604/193 |

Primary Examiner—C. Fred Rosenbaum
Assistant Examiner—Chalin Smith
Attorney, Agent, or Firm—William J. Davis

[57] ABSTRACT

A self-packaging safety syringe set (2) uses a unitary molded set of enclosure units (8, 104) sized for housing conventional cartridge-needle units (12) therein. The set of enclosure units are connected to one another by frangible connections (64, 66; 130, 138). The cartridge-needle unit has a hollow barrel (14) with a needle assembly (24) mounted to one end and a piston (16) mounted therein. Each enclosure unit includes a body section (38, 106), a stem section (44, 108) frangibly connected to one end of the body section, and an end cap (52, 110) connected to the other end of the body section. The frangible connection (48, 118) is broken to remove the stem section to expose the needle (26) for use. The removed stem section is used to drive the piston within the barrel. After use, the barrel is pulled back through the body section so that the needle is completely housed within the body section. At that point radially inwardly extending spring fingers (84, 132) engage a shoulder (76) on the hub (34) of the needle assembly to keep the needle assembly from being withdrawn from the body section to permit a safe disposal of the used syringe. The syringe set needs no special packaging and no holders for the cartridge-needle units, the enclosure units serving as both.

7 Claims, 5 Drawing Sheets

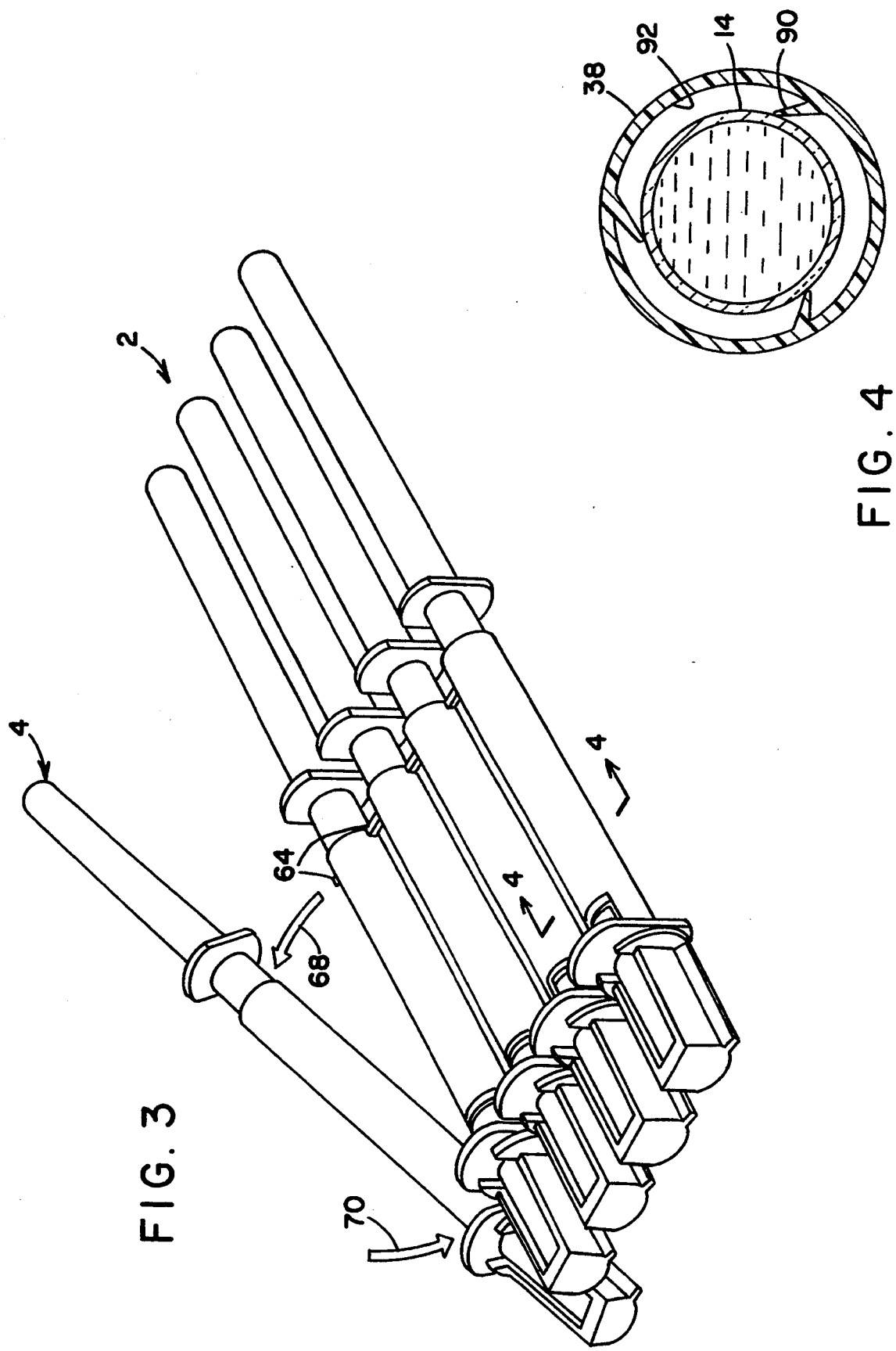

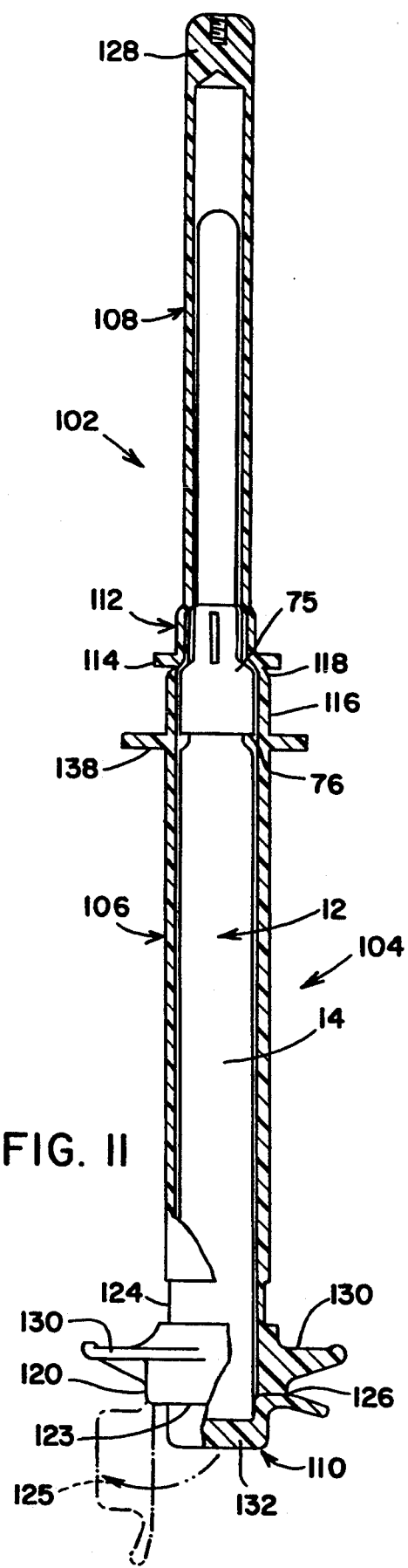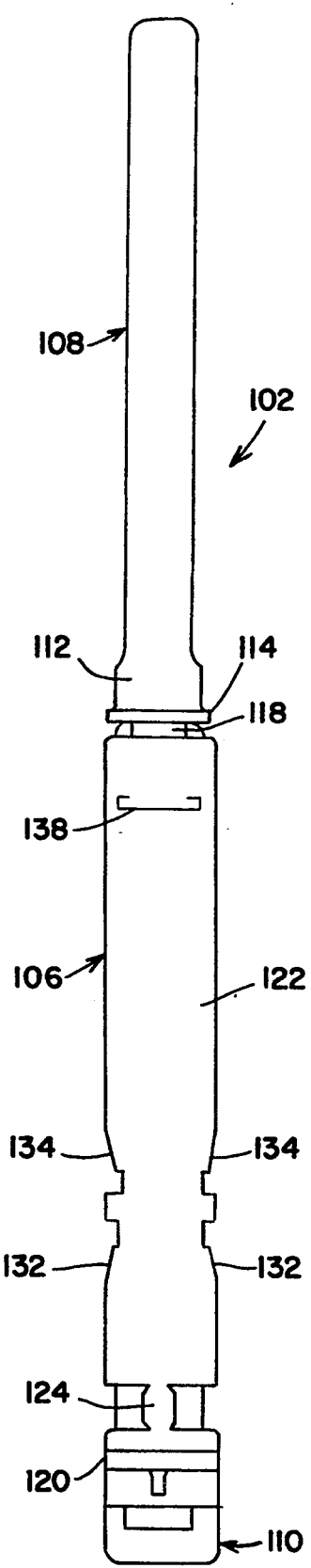
FIG. 11
FIG. 12

MULTI-CELLED SAFETY PACKAGE, NEEDLE GUARD AND SAFE DISPOSAL MODULE FOR PRE-FILLED MEDICATION CARTRIDGES

This application is a division of U.S. patent application Ser. No. 08/153,945 filed Nov. 16, 1993 now U.S. Pat. No. 5,324,272, which is a continuation of U.S. patent application Ser. No. 07/973,582 filed Nov. 6, 1992, now abandoned, which is a continuation of U.S. patent application Ser. No. 07/558,878, filed Jul. 27, 1990 now abandoned.

BACKGROUND OF THE INVENTION

Many medications are provided in fixed dosage cartridge-needle units. Cartridge-needle units include a glass barrel to which a needle assembly is mounted at one end. The barrel is filled with a medicine. The medicine is held within the barrel by a piston at one end and, typically, a rubber diaphragm at the needle end. The needle assembly is typically mounted to a necked down region of the barrel by a hub. The inner end of the needle is mounted within the hub to a position just opposite the rubber diaphragm. To activate the cartridge-needle unit, the barrel and needle assembly are pushed towards one another so that the inner end of the needle punctures the diaphragm to allow the medicine within the barrel to flow through the needle.

Cartridge-needle units are commonly used with a reusable holder. Holders have a body within which the cartridge-needle unit is placed. The holder includes a stem or plunger which is mounted, typically threaded, to the piston. The sheath covering the needle is removed and the injection is given. After use, the plunger is uncoupled from the piston and the used cartridge-needle unit is removed from the body and disposed of.

While the use of cartridge-needle units has many advantages, there are drawbacks as well. Several cartridge-needle units are generally packaged in a tamper resistant container. Often the container will use a metal shield at the plunger ends of the barrels to keep unscrupulous individuals from surreptitiously gaining access to the contents of the unit. The special packaging used is relatively costly and increases the actual cost of each cartridge-needle unit. Further, the present systems are not well suited for preventing inadvertent needle sticks, a serious health concern.

SUMMARY OF THE INVENTION

The present invention is directed to an enclosure unit specially adapted for use with conventional cartridge-needle units to create a low-cost disposable safety syringe. Several of the enclosure units can be molded as a set which act as the packaging for the cartridge-needle units. The syringes can be separated for use at frangible attachment points connecting the enclosure units.

The cartridge-needle unit is of the type having a hollow barrel with a needle assembly mounted to one end and a piston mounted within the hollow barrel. The enclosure unit includes a body section sized to house the barrel, a stem section at one end of the barrel sized to house the needle assembly, and an end section or cap at the other end of the body section. The enclosure unit is preferably a one-piece molded item with the end cap connected to the body section by hinge. The stem section is frangibly attached to the body section so that it can be removed to expose the needle for use. The tip of the removed stem section is connected to the piston to move the piston within the barrel during use.

After use, the barrel of the cartridge-needle unit is pulled back through the body section so that the needle is completely housed within the body section. The body section includes one or more radially inwardly extending spring fingers, or like structure, near the plunger end of the body section. The spring fingers engage the hub of the needle assembly and keep the needle assembly from being withdrawn from the body section. This permits a safe disposal of a used syringe.

The enclosure is preferably molded as a set of enclosure units connected to one another by frangible connections. A set of conventional cartridge-needle units can thus be placed within each of the enclosure units in the set for storage, shipping and distribution to the end user. The syringe set needs no special packaging, thus substantially reducing cost.

One of the primary advantages of the invention is that it eliminates the need for separate, and costly, safety packaging for cartridge-needle units. The enclosure units not only provide safety packaging but also eliminate the need for cartridge-needle unit holders when dispensing the medication. In addition, the enclosure unit is adapted to permit the needle to be withdrawn into the body section of the enclosure unit for safe disposal after use. These advantages are all achieved at relatively low cost through the use of enclosure units made of one, or preferably at most two, molded parts without requiring any substantial modification of conventional cartridge-needle units.

The invention can be carried out using an enclosure unit in which the internal diameter along at least one-third of the length of the body section from its needle end is a constant diameter. This eliminates any shoulder or other inward projection which would prevent the cartridge-needle unit from passing through the opening at the needle end once the stem section has been removed. To accommodate this, the plunger end of the body section is secured to the barrel of the cartridge-needle unit, such as with a friction fit or using an adhesive. To permit conventional cartridge-needle units to be activated, the plunger end of the body section is connected to the remainder of the body section by, preferably, a pair of relatively thin, flexible teathers; this permits the plunger end to be pushed toward the remainder of the body section, thus driving the barrel towards the needle assembly prior to removing the stem section. After the injection is given, the plunger end is twisted causing the teathers to break. This permits the user to pull the barrel from the body section until the spring fingers engage the annular recess adjacent the rear shoulder of the hub, thus halting movement as with the embodiment described above.

The invention is intended for use with conventional cartridge-needle units, which are made to be sterile. Therefore, the enclosure unit need not be sterile, thus reducing cost.

Other features and advantages of the invention will appear from the following description in which the preferred embodiments have been set forth in detail in conjunction with the accompanying drawings.

BRIEF DESCRIPTION OF THE DRAWINGS

FIG. 3 is a perspective view of a syringe set of FIG. 1 after assembly with the end sections of the enclosure units covering the plunger ends of the barrels of the cartridge-needle units and illustrating breaking the frangible connections between two adjacent syringes;

FIG. 4 is a cross-sectional view taken along line 4—4 of FIG. 3, showing the flexible centering tabs which accommodate different size barrels;

FIG. 11 is a front, partial cross-sectional view of an alternative embodiment of the safety syringe of FIG. 3; and FIG. 12 is a right side view of the safety syringe of FIG. 11.

DESCRIPTION OF THE PREFERRED EMBODIMENT

Figures 1, 2:
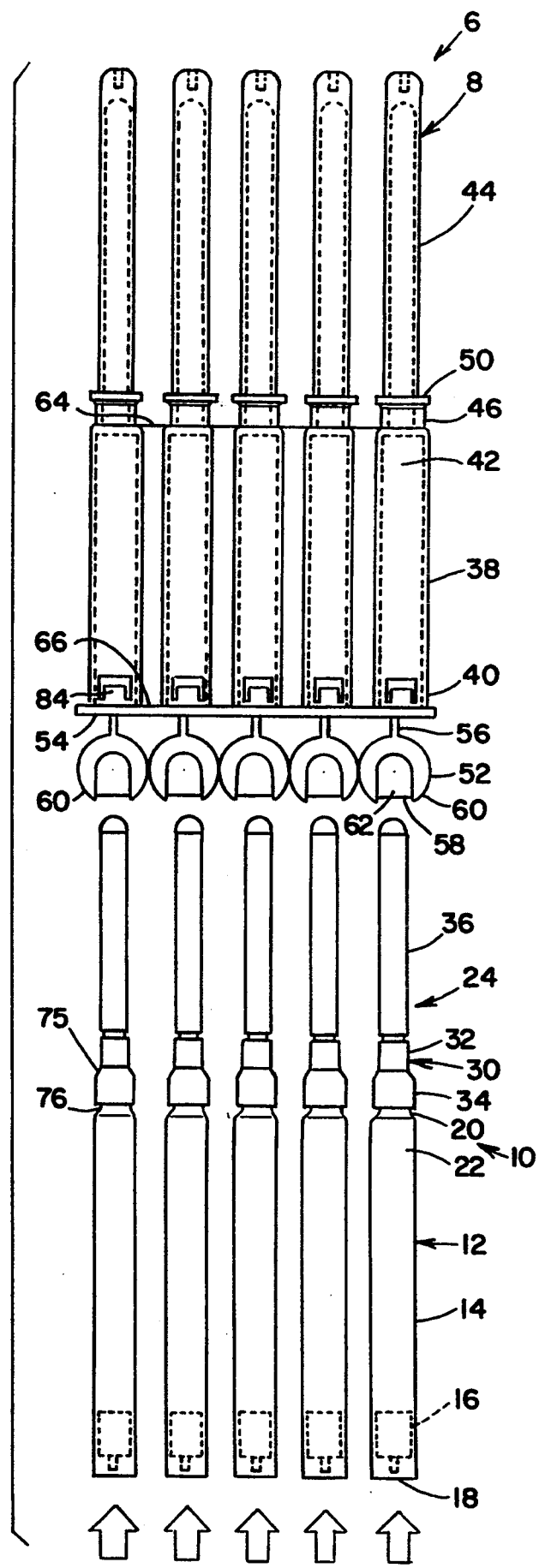
FIG. 1 is a front view showing an enclosure unit set and an associated set of cartridge-needle units prior to insertion of the cartridge-needle units into the hollow interiors of the enclosure units.
FIG. 2 is a side view of an enclosure unit of FIG. 1 illustrating the hinged connection of the end section of the enclosure unit to the body section of the enclosure unit.

FIG. 3 illustrates a set 2 of safety syringes 4. Set 2, as suggested in FIG. 1, is made up of a set 6 of enclosure units 8 and a set 10 of cartridge-needle units 12. Cartridge-needle units 12 are preferably generally conventional in construction. One such cartridge-needle unit is made by Winthrop Brean of New York, N.Y. under the trademark CARPUJECT. Each unit 12 includes a glass barrel 14 having a piston 16 at a plunger end 18 and a necked down portion 20 at a needle end 22. A needle assembly 24 is mounted to necked down portion 20 of barrel 14. Needle assembly 24 includes a needle 26, see FIG. 8, mounted to an extension 28 of a needle mount 30. Needle mount 30 includes a ribbed coupler 32 and a hub 34. Needle assembly 24 is mounted to necked down portion 20 by needle mount 30 at hub 34. Needle 26 is covered by a removable sheath 36.

Enclosure unit 8 includes a hollow body section 38 having a plunger end 40 and a needle end 42. Unit 8 also includes a stem section 44 extending from a necked down portion 46 of body section 38 at needle end 42. Stem section 44 is also hollow and is sized to enclose sheath 36 covering needle 26. Body section 38 and stem section 44 are a one-piece molding connected at frangible connections 48 adjacent a flange 50 at the base of stem section 44 and necked down portion 46 at the end of body section 38.

Enclosure unit 8 also includes an end section or cap 52. In the preferred embodiment of set 6 of enclosure units 8, enclosure units 8, including body section 38, stem section 44 and cap 52, is a one-piece molded item. Caps 52 are connected to flanges 54 at plunger ends 40 of body sections 38 by hinges 56. Since the entire barrel 14 does not fit within body section 38, but a portion extends past the plunger end 40, pivotal end section 52 has a open side 58 to permit end section 52 to be pivoted over plunger end 18 of barrel 14. After doing so, a flange 60 of end section 52 is secured to flange 54 at plunger end 40, such as by ultrasonic welding techniques.

Set 2 of safety syringes 4 are thus provided with their own safety packaging in the form of set 6 of enclosure units 8. Specialized and costly packaging for units 12 is not needed. Tampering is discouraged since any tampering would be evident by the resulting breaking of frangible connections in the bond between flanges 52, 56. Further, the ends 62 of end sections 52 are relatively thick plastic to substantially prevent unauthorized access to pistons while cap 52 is in the closed or sealed position of FIG. 3.

Enclosure units 8 are connected to one another at frangible connections 64,66. To use a safety syringe 4, the safety syringe is removed from the remaining safety syringes by severing frangible connections 64,66 as illustrated by arrows 68,70 in FIG. 3.

Figure 5:
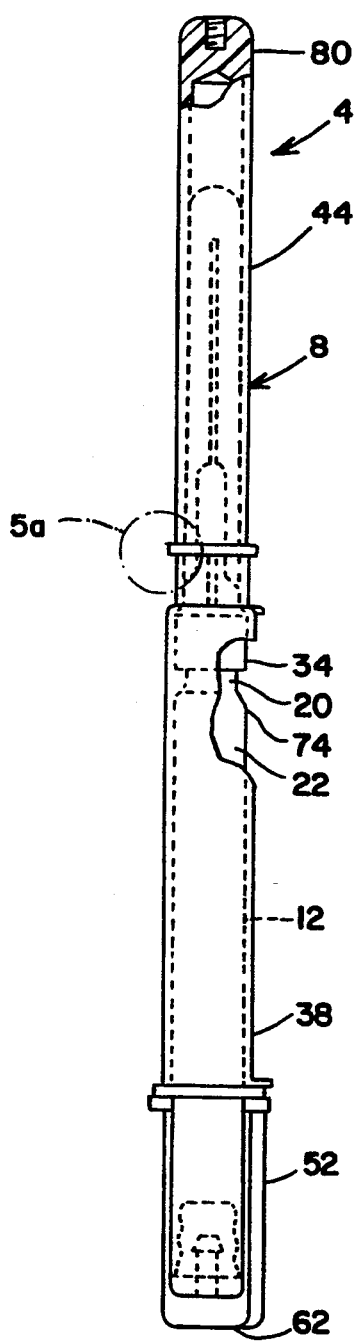
FIG. 5 is a front view of the safety syringe of FIG. 3, illustrating various components of the cartridge-needle unit in dashed lines and with a portion of the stem section of the enclosure unit broken away to show internal detail.

FIG. 5 is a front view of the safety syringe 4 of FIG. 3. The various components of cartridge-needle unit 12 are shown in dashed lines to illustrate their relative positions within enclosure 8.

Figure 6:
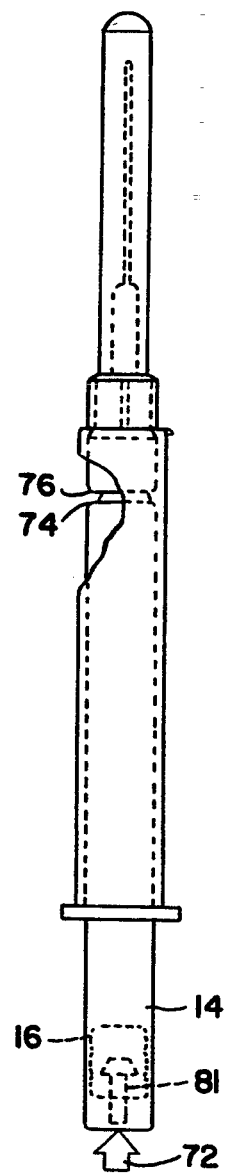
FIG. 6 illustrates the safety syringe of FIG. 5 with the stem and end sections removed from the body section and illustrating the activation of the cartridge-needle unit by pushing the plunger end of the barrel into the body section.
Figure 5A:
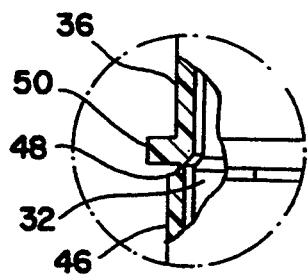
FIG. 5A is an enlarged view showing the frangible connection between the stem and body sections of the enclosure unit of FIG. 5.
Figure 7:
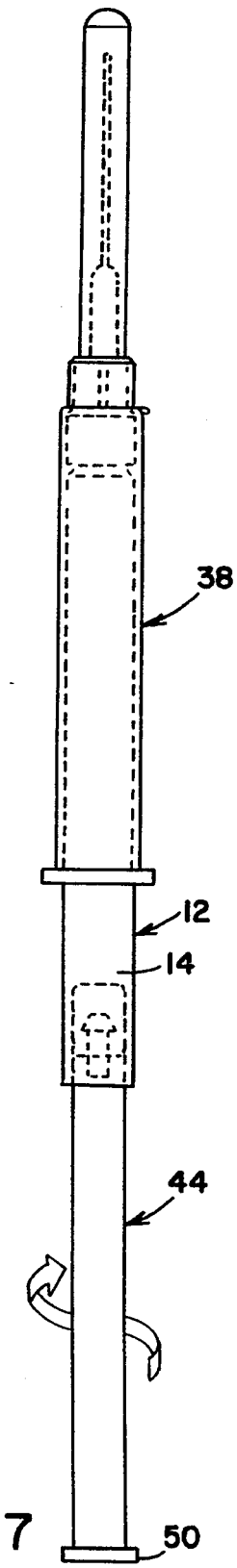
FIG. 7 illustrates mounting the tip of the stem section to the threaded mounting post of the plunger.
Figure 10:
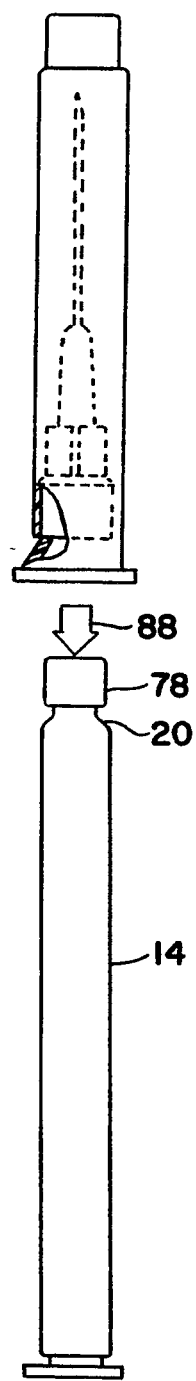
FIG. 10 illustrates the disengagement of the barrel of the cartridge-needle unit from the hub of the needle assembly for disposal.

FIG. 6 illustrates safety syringe 4 of FIG. 5 with stem section 44 removed through the breaking of frangible connections 48 illustrated in FIG. 5A. Also, FIG. 6 suggests the axial movement of barrel 14 in the direction of arrow 72 thus activating cartridge-needle unit 12. This movement is suggested by the change in the size of the annular recess 74 formed at the rear shoulder 76 of hub 34 and necked down portion 20 of barrel 14 at needle end 22. (Compare FIGS. 5 and 6.) Hub 34 of needle assembly 24 is prevented from moving in the direction of arrow 72 by the engagement of a front shoulder 75 of hub 34 with a shoulder 77 of body section 38 adjacent necked down portion 46. With the particular cartridge-needle unit 12 used in this embodiment, such movement permits the base end, not shown, of needle 26 to puncture a diaphragm, not shown, carried by an end cap 78, shown in FIG. 10, mounted to necked down portion 20. Doing so permits the contents of barrel 14 to flow through needle 26 when piston 16 is forced through barrel 14. To do so, the threaded tip 80 of stem section 44 is mounted to a threaded mounting post 81 extending from piston 16 as suggested in FIG. 7. Stem section 44 with its flange 50 acts as a stem or plunger for delivery of the contents of barrel 14 through needle 26.

Figure 8:
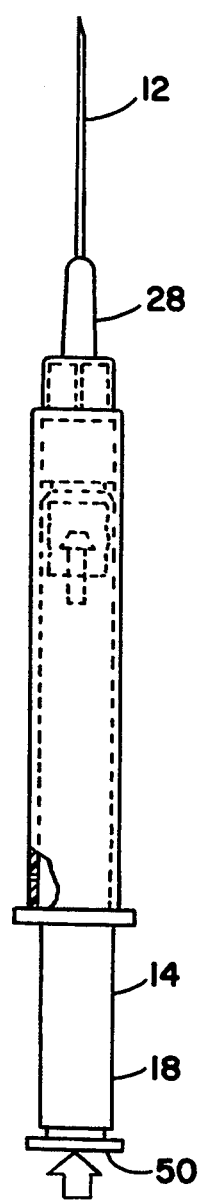
FIG. 8 illustrates the safety syringe of FIG. 7 after the sheath has been removed and the injection has been given.
Figure 9:
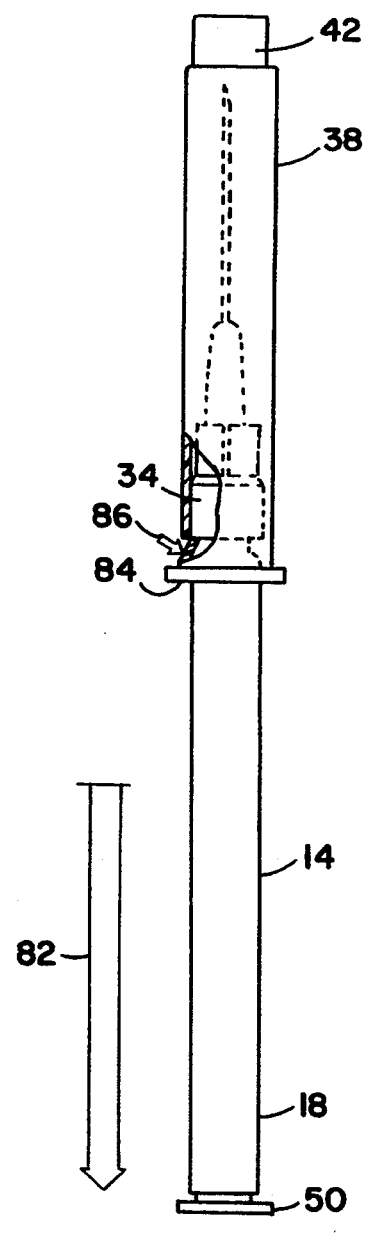
FIG. 9 illustrates the withdrawal of the barrel from the body section until the rear shoulder of the hub engages the inwardly extending spring finger adjacent the plunger end of the body section, the spring finger located so that the entire needle is within the body section at this position.

FIG. 8 illustrates stem section 44 fully within barrel 14 with the contents of barrel 14 fully delivered. Though the spent syringe could be disposed of as is, it may be dangerous to do so with needle 26 exposed. To place needle 26 in its safe position, the user needle grasps the plunger end 18 of barrel 14 and pulls in the direction of arrow 82. When barrel 14 reaches the position of FIG. 9, an inwardly biased spring finger 84, formed as part of body section 38, pivots inwardly as suggested by arrow 86 to enter annular recess 74 and engage rear shoulder 76 of hub 34. This prevents the further withdrawal of needle assembly 24 (minus sheath 36) from body section 38. The syringe unit in the safe position of FIG. 9 can be disposed as is. With the particular cartridge-needle unit 12 of the preferred embodiment, further movement of barrel 14 in the direction or arrow 88, see FIG. 10, causes the disengagement of end cap 78 from within hub 34 so that the used syringe can be disposed of as two components, but in a safe manner.

FIG. 4 illustrates the provision of three resilient centering tabs 90 extending from the inner surface 92 of body section 38 adjacent spring finger 84. Centering tabs 90 center barrel 14 and also keep cartridge-needle unit 12 from slipping out plunger end 40 of body section 38 when end section 52 is removed. Centering tabs 90 likewise engage hub 34 when the needle is in the safe position of FIGS. 9 and 10 to keep the needle from inadvertently moving back through the open needle end 42 of body section 38.

FIGS. 11 and 12 show an alternative embodiment of the safety syringe 4. Syringe 102 uses cartridge-needle unit 12. Safety syringe 102 includes an enclosure unit 104 having a body section 106, a stem section 108 and an end section or cap 110. Enclosure unit 104 is similar to enclosure unit 8 but with the distinctions described below. With the embodiment of FIG. 1, necked down portion 46 is a part of body section 38. With the embodiment of FIG. 11, an intermediate diameter portion 112 is a part of stem section 108. A flange 114 is at the base of stem section 108 and is between intermediate diameter portion 112 and the needle end 116 of body section 106. The connection between stem section 108 and body section 106 is through frangible connections 118. Once stem section 108 is removed, typically by twisting relative to body section 106, the inner diameter of body section 106 from its needle end 116 rearwardly, that is, towards end section 110, is a constant diameter for at least one-third of the length of body section 106.

To keep cartridge-needle unit 12 from falling out of open needle end 116 once stem section 108 has been removed, plunger end 120 of body section 106 is secured to plunger end 18 of barrel 14. This can be by frictional engagement, by use of an adhesive, or similar means. The plunger end 120 of body section 106 is secured to the remainder 122 of body section 106 by a pair of flexible teathers 124. Teathers 124 are flexible enough to permit plunger end 120 to be driven towards remainder 122 when it is desired to activate cartridge-needle unit 12. Once this is done, stem section 108 is removed and end section 110 is pivoted about hinge 123 in the direction of arrow 125, thus breaking the heat seal at 126. This provides access to piston 16 so that the threaded tip 128 of stem section 108 can be secured to the threaded mounting post 82 of piston 16 to deliver the contents of barrel 14.

To pull needle 26 back into body section 106, the user grasps radially extending ears 130 extending from plunger end 120 and twists to sever the frangible connections at teathers 124. Barrel 14 is then pulled back through body section 106 until rear shoulder 76 contacts first spring fingers 132. Continued pulling of plunger end 120 causes barrel 14 to be separated from hub 34 as in FIG. 10. A second pair of spring fingers 134 engage the front shoulder 75 of hub 34 to substantially prevent the inadvertent movement of needle 26 back through open needle end 116. The tapered shape of front shoulder 75 allows the insertion of cartridge-needle unit 12 into body section 106 but supplies sufficient retarding force to keep the needle within body section 106 after use.

As with end section 52, end section 110 has a thick end 132, typically 2.5 mm thick. Making enclosure units 8, 104 of a suitable plastic, such as polypropylene or polyethylene, provides the necessary resilience and strength at a reasonable price. Enclosure unit 104 is preferably provided as a set of enclosure units with the frangible connections through ears 130 and frangible connecting pieces 138. Cartridge-needle units 12 are preferably of the type in which axial movement is undertaken to activate the unit; however, cartridge-needle units which do not need such activation may be used as well. In such cases, teathers 124 could be replaced by simple frangible connections. Although it is desired that conventional cartridge-needle units 12 be used, some small modifications may be desirable. For example, the diameter of all or most of sheath 36 may be reduced to permit an increase in the wall thickness of stem section 44 used as the plunger stem. Other modifications and variations can be made to the disclosed embodiments without departing from the subject of the invention as defined in the following claims.

What is claimed is:

1. A safety syringe comprising:
   a prefilled cartridge-needle unit including a hollow barrel having a plunger end and a needle end, a piston mounted within the barrel, and a needle assembly, including a needle, mounted to the needle end; and
   a hollow enclosure unit sized for housing the cartridge-needle unit therein for movement between safe and use positions regardless of the relative rotary orientations of the cartridge-needle unit and the enclosure unit, the enclosure unit comprising:
   a body section housing the barrel, the body section having a plunger end and a needle end;
   a stem section attached to the body section;
   an end section attached to the body section to cover the plunger end of the barrel assembly;
   the stem section being separable from the body section and the end section being at least partially separable from the body section; and
   the stem section configured to drive the piston along the barrel after the end section has been at least partially separated from the body section to expose the plunger end of the barrel assembly;
   said needle assembly including a hub having a radially extending rear shoulder facing the plunger end of the barrel and a front shoulder facing away from the rear shoulder;
   said body section including an inwardly extending first spring finger configured to engage the rear shoulder when the cartridge-needle unit is at a safe position partially withdrawn from the plunger end of the body section, said first spring finger positioned to engage said rear shoulder after the needle is fully within the body section to restrict removal of the needle assembly from the plunger end of the body section to help prevent inadvertent needle sticks;
   and wherein the body section includes a second inwardly extending spring finger configured to engage the front shoulder when the cartridge needle unit is in the safe position to restrict movement of the needle assembly back through the needle end of the body section to help prevent inadvertent needle sticks.

2. A hollow enclosure unit sized for housing a prefilled cartridge-needle unit therein for movement between safe and use positions regardless of the relative rotary orientations of the cartridge-needle unit and the enclosure unit, the cartridge-needle unit including a hollow barrel, having a plunger end and a needle end, a piston mounted within the barrel, and a needle assembly, including a needle, mounted to the needle end, the enclosure unit comprising:

a body section sized for housing the barrel, the body section having a plunger end and a needle end;

a stem section attached to the body section;

an end section attached to the body section and sized for covering the plunger end of the barrel assembly;

the stem section being separable from the body section and the end section being at least partially separable from the body section;

the stem section configured to drive the piston along the barrel after the end section has been at least partially separated from the body section to expose the plunger end of the barrel assembly; and wherein a portion of the plunger end of the body section is secured to the barrel to prevent the cartridge-needle unit from passing through the needle end of the body section after the stem section has been removed from the body section.

3. The unit of claim 2 wherein said portion of the plunger end of the body section is frangibly connected to the remainder of the body section to permit the cartridge-needle unit to be at least partially withdrawn from said remainder of the body section through the plunger end so to position the needle assembly at a safe position with the needle entirely within the body section.

4. The unit of claim 3 further comprising means for securing the needle assembly at said safe position.

5. The unit of claim 2 wherein said portion of the plunger end of the body section is secured to the remainder of the body section by flexible teathers which permits said portion of the plunger end of the body section to move axially relative to said remainder of the body section to permit the barrel to be moved axially towards the needle assembly.

6. The unit of claim 1 wherein said portion of the plunger end of the body section is secured to the remainder of the body section by flexible teathers which permits said portion of the plunger end of the body section to move axially relative to said remainder of the body section to permit the barrel to be moved axially towards the needle assembly.

7. The unit of claim 6 further comprising an external gripping region at said portion of the plunger end of the body section, said gripping region sized to allow the user to twist said plunger portion relative to the remainder of the body section so to break the flexible tether and permit the user to position the needle assembly at said safe position.

* * * * *